(12) United States Patent
Lee et al.

(10) Patent No.: US 9,782,760 B2
(45) Date of Patent: Oct. 10, 2017

(54) METHOD OF PREPARING AN ACTIVATED EU-2 ZEOLITE

(71) Applicants: SK INNOVATION CO., LTD., Seoul (KR); SK LUBRICANTS CO., LTD., Seoul (KR)

(72) Inventors: Yoon Kyung Lee, Chungcheongbuk-do (KR); Seung Woo Lee, Daejeon (KR); Jae Suk Choi, Daejeon (KR); Tae Jin Kim, Seoul (KR); Do Woan Kim, Daejeon (KR); Seon Ju Lim, Daejeon (KR)

(73) Assignees: SK INNOVATION CO., LTD., Seoul (KR); SK LUBRICANTS CO., LTD., Seoul (KR)

( * ) Notice: Subject to any disclaimer, the term of this patent is extended or adjusted under 35 U.S.C. 154(b) by 0 days.

(21) Appl. No.: 15/605,156

(22) Filed: May 25, 2017

(65) Prior Publication Data
US 2017/0259251 A1    Sep. 14, 2017

Related U.S. Application Data

(62) Division of application No. 14/517,583, filed on Oct. 17, 2014.

(30) Foreign Application Priority Data

Oct. 18, 2013 (KR) ........................ 10-2013-0124678

(51) Int. Cl.
| | | |
|---|---|---|
| *B01J 29/06* | (2006.01) | |
| *B01J 29/70* | (2006.01) | |
| *B01J 29/78* | (2006.01) | |
| *C07C 5/27* | (2006.01) | |
| *B01J 29/74* | (2006.01) | |
| *B01J 35/10* | (2006.01) | |
| *C10G 45/64* | (2006.01) | |
| *B01J 29/76* | (2006.01) | |
| *B01J 29/04* | (2006.01) | |

(52) U.S. Cl.
CPC ......... *B01J 29/7023* (2013.01); *B01J 29/041* (2013.01); *B01J 29/043* (2013.01); *B01J 29/044* (2013.01); *B01J 29/045* (2013.01); *B01J 29/703* (2013.01); *B01J 29/74* (2013.01); *B01J 29/7461* (2013.01); *B01J 29/76* (2013.01); *B01J 29/7661* (2013.01); *B01J 29/78* (2013.01); *B01J 29/7846* (2013.01); *B01J 29/7861* (2013.01); *B01J 35/1019* (2013.01); *B01J 35/1038* (2013.01); *C07C 5/2775* (2013.01); *C10G 45/64* (2013.01); *B01J 35/108* (2013.01); *B01J 35/109* (2013.01); *B01J 35/1042* (2013.01); *B01J 35/1057* (2013.01); *B01J 35/1061* (2013.01); *B01J 35/1095* (2013.01); *B01J 2229/10* (2013.01); *B01J 2229/14* (2013.01); *B01J 2229/186* (2013.01); *B01J 2229/20* (2013.01); *B01J 2229/26* (2013.01); *B01J 2229/38* (2013.01); *B01J 2229/42* (2013.01); *C07C 2529/06* (2013.01); *C07C 2529/068* (2013.01); *C07C 2529/072* (2013.01); *C07C 2529/70* (2013.01); *C07C 2529/74* (2013.01); *C07C 2529/76* (2013.01)

(58) Field of Classification Search
CPC . B01J 29/045; B01J 29/74; B01J 29/76; B01J 29/78; B01J 29/041; B01J 29/043; B01J 29/044; B01J 29/703; B01J 29/7461; B01J 29/7661; B01J 29/7861; B01J 35/108; B01J 35/109; B01J 35/1042; B01J 35/1057; B01J 35/1061; B01J 35/1038; B01J 2229/10; B01J 2229/38; C07C 2529/06; C07C 2529/068; C07C 2529/072; C07C 2529/70; C07C 2529/74; C07C 2529/76
USPC ........................................ 502/60, 66, 74, 85
See application file for complete search history.

(56) References Cited

U.S. PATENT DOCUMENTS

| | | | | |
|---|---|---|---|---|
| 3,140,249 A | * | 7/1964 | Rosinski | ................... B01J 20/18 208/120.01 |
| 3,140,251 A | * | 7/1964 | Rosinski | ................ B01J 29/061 208/120.01 |
| 3,326,797 A | * | 6/1967 | Young | .................... B01J 20/186 208/111.35 |
| 4,741,891 A | * | 5/1988 | Casci | ....................... B01J 29/70 423/326 |

(Continued)

FOREIGN PATENT DOCUMENTS

| | | | |
|---|---|---|---|
| EP | 2559483 | * | 3/2013 |
| KR | 20140067323 | * | 6/2014 |
| WO | 2012055755 | * | 5/2012 |

OTHER PUBLICATIONS

Araya et al., "A Partial Determination of the Stability Fields of Ferrierite and Zeolites ZSM-5, ZSM-48 and NU-10 in the K2O-Al2O3-SiO2NH2[CH2]6NH2 System", J. Chem Research, 1985, p. 192-193.*

(Continued)

*Primary Examiner* — Elizabeth Wood
(74) *Attorney, Agent, or Firm* — Abelman, Frayne & Schwab

(57) ABSTRACT

Disclosed herein is a method of making activated EU-2 zeolite, including: pores having a diameter of 30 to 40 Å while maintaining the crystal structure of the EU-2 zeolite; and pores having a diameter of 40 to 200 Å, wherein the volume of the pores having a diameter of 30 to 40 Å is 0.01 to 0.06 cc/g, and the volume of the pores having a diameter of 40 to 200 Å is 0.07 to 0.4 cc/g.

9 Claims, 3 Drawing Sheets

(56) References Cited

U.S. PATENT DOCUMENTS

| | | | | |
|---|---|---|---|---|
| 4,836,996 | A * | 6/1989 | Casci | B01J 29/70 423/277 |
| 4,876,412 | A * | 10/1989 | Casci | B01J 29/70 210/691 |
| 5,098,685 | A * | 3/1992 | Casci | B01J 29/70 423/708 |
| 6,923,949 | B1 * | 8/2005 | Lai | C01B 39/48 423/705 |
| 6,984,309 | B2 * | 1/2006 | Benazzi | B01J 29/74 208/108 |
| 7,482,300 | B2 * | 1/2009 | Lai | B01J 29/703 502/60 |
| 2005/0040073 | A1 | 2/2005 | Cody | C10G 65/043 208/89 |
| 2012/0018349 | A1 * | 1/2012 | Van Donk | B01J 29/084 208/109 |
| 2013/0037446 | A1 * | 2/2013 | Minoux | B01J 29/06 208/64 |
| 2013/0288885 | A1 * | 10/2013 | Domokos | B01J 23/42 502/77 |
| 2014/0296596 | A1 * | 10/2014 | Chaumonnot | B01J 29/0308 585/324 |

OTHER PUBLICATIONS

Liu, Xiaoling et al., "Synthesis and Characterization of Hierarchical ZSM-48 Zeolite", Advanced Materials Research, vol. 503-504, 2012, pp. 758-759.*

Groen, J. C. et al., "On the introduction of intracrystalline mesoporosity in zeolites upon sesilication in alkaline medium", Microporous and Mesoporous Materials, vol. 69, No. 1-2, pp. 29-34, 2004.*

Van Laak, Adri N. C. et al., "Alkaline treatment of template containing zeolites: Introducing mesoporosity while preserving acidity", Catalysis Today, vol. 168, No. 1, pp. 49-56, 2010.*

Jo, Changbum, et al., "Mesopore expansion of surfactant-directed nanomorphic zeolites with trimethylvenzene", Microporous and Mesoporous Materials, vol. 194, pp. 83-89, 2014.*

European Search Report for EP 14 18 9137, May 28, 2015, 13 pages.*

Goto et al., "Mesoporous Material from Zeolite", Journal of Porous Materials, 9, pp. 43-48, 2002.*

Zhang et al., "Creating mesopores in ZSM-48 by alkali treatment: Enhanced catalyst for hydroisomerization of hexadecane", Journal of Energy Chemistry, 25, pp. 539-544, 2016.*

* cited by examiner

METHOD OF PREPARING AN ACTIVATED EU-2 ZEOLITE

CROSS REFERENCE TO RELATED APPLICATION(S)

This application is a divisional application of co-pending U.S. patent application Ser. No. 14/517,583, which claims the benefit under 35 USC §119 of Korean Patent Application No. 10-2013-0124678, filed on Oct. 18, 2013, entitled "Activated EU-2 Zeolite and Use Thereof", which are hereby incorporated by reference in their entireties into this application.

BACKGROUND OF THE INVENTION

1. Technical Field

The present invention relates to an activated EU-2 zeolite and use thereof. More particularly, the present invention relates to an EU-2 zeolite, the activity thereof for a hydroisomerization reaction (particularly, a reaction for converting n-paraffin into iso-paraffin) is improved by increasing pores with specific sizes while maintaining the crystal structure thereof, a method of preparing the same, and a method of hydroisomerizing or hydrodewaxing various hydrocarbon fractions using the EU-2 zeolite.

2. Description of the Related Art

In an oil refining process for producing lube oil, diesel oil and the like, a hydroisomerization reaction for converting n-paraffin into iso-paraffin becomes more important. The reason for this is that n-paraffin does not meet the recently required standards of fuel oil and lube oil products because long-chain n-paraffins show the poor cold flow properties. Particularly, recently, the quality of raw materials has been deteriorated by the influence of rise of oil price, but on the other hand, high-quality fuel oil and lube oil products have been required with the advancement of automobile engine technologies. For example, the hydroisomerization reaction can be put to practical use in a process of producing gasoline with a high octane number gasoline using hydrocarbons of C4-C7, a process of producing high-quality diesels with high cetane number having improved cold flow properties using hydrocarbons of C7-C15 and a process of producing high-grade lube oil having a high viscosity index using n-paraffin of C15 or more.

This hydroisomerization reaction is known to be generally performed by a bi-functional catalyst. Here, the bi-functional catalyst is composed of a metal composition having functions for hydrogenation/dehydrogenation and a support having acid sites for skeletal isomerization. In relation to this, various materials, such as silica-alumina, clay and zeolite, are known as a support having acid sites. Particularly, among these materials, zeolite is suitable for a hydroisomerization reaction because it has a stable structure even under severe reaction conditions and has a large surface area and a large number of acid sites.

It was reported that researches into zeolite materials having excellent shape selectivity for maximizing a hydroisomerization reaction and inhibiting the cracking of hydrocarbons (feedstocks) have been made, and, among these zeolite materials, zeolite materials (ZSM-22, ZSM-23, EU-2, ZSM-48 and the like) having a uni-dimensional 10-ring pore structure had excellent selectivity to a hydroisomerization reaction.

According to the catalog of International Zeolite Association (IZA), EU-2 belongs to the ZSM-48 family together with ZSM-48, ZBM-30 and EU-11. These zeolites have similar XRD patterns, that is, crystal structures.

As described above, U.S. Pat. No. 6,984,309 discloses a technology for improving paraffin properties (particularly, viscosity index, pour point, etc.) of hydrocarbon fractions by performing a hydroisomerization reaction in the presence of a catalyst including EU-2 (or EU-2 and a binder) as a support and supported with a hydrogenated metal. However, this technology corresponds to a technology for changing the distribution characteristics of supported precious metal particles rather than changing the properties of EU-2 itself.

Meanwhile, technologies for improving hydroisomerization performance by reforming the properties of EU-2 itself are also known.

As typical examples of such technologies, U.S. Pat. Nos. 6,923,949 and 7,482,300 disclose a zeolite synthesis method for improving the purity of a crystal structure of ZSM-48 belonging to the same family as EU-2 under the usage of specific seeds or under the absence of seeds. Further, it is disclosed in the Patent documents that the zeolite ZSM-48 manufactured by this method can exhibit improved hydroisomerization effects.

Meanwhile, as a technology for improving catalytic performance by reforming the previously-synthesized EU-2 zeolite by particular post-treatment, WO2012/055755 A1 discloses a catalyst, the hydroconversion activity (particularly, dewaxing activity) of which is improved by bringing EU-2 zeolite into contact with a solution containing an organic acid of 2 to 6 carbon atoms, particularly, a fluorine-containing salt. In this case, most of the above-mentioned conventional technologies are based on EU-2 zeolite having pores of 30 to 40 Å.

However, in order to meet the requirements for hydroisomerization or hydrodewaxing activity, it is additionally required to improve the properties of EU-2 itself.

SUMMARY OF THE INVENTION

Accordingly, the present invention has been devised to solve the above-mentioned problems, and the present invention intends to provide an activated EU-2 zeolite, the activity thereof for a hydroisomerization reaction is improved by developing pores having a predetermined pore size while maintaining the crystal structure thereof similar to that of conventional EU-2 zeolite, and a method of preparing the same.

Further, the present invention intends to provide a catalyst containing the activated EU-2 zeolite and a method of hydroisomerizing hydrocarbon fractions using the catalyst.

In order to accomplish the above objects, a first aspect of the present invention provides an activated EU-2 zeolite, including: pores having a diameter of 30 to 40 Å while maintaining the crystal structure of the EU-2 zeolite; and pores having a diameter of 40 to 200 Å, wherein the volume of the pores having a diameter of 30 to 40 Å is about 0.01 to 0.06 cc/g, and the volume of the pores having a diameter of 40 to 200 Å is about 0.07 to 0.4 cc/g.

According to an embodiment, the activated EU-2 zeolite may further include: pores having a diameter of more than 200 Å, wherein the volume of the pores having a diameter of more than 200 Å is about 0.1 cc/g or less.

According to an embodiment, the total specific surface area of the activated EU-2 zeolite may be 240 to 330 m²/g.

A second aspect of the present invention provides a method of preparing an activated EU-2 zeolite, including the steps of: a) hydrothermally synthesizing an EU-2 zeolite; and b) activating the EU-2 zeolite by bringing the EU-2 zeolite into contact with an aqueous alkali solution before or after calcining the EU-2 zeolite, wherein the activated EU-2 zeolite comprises: pores having a diameter of 30 to 40 Å while maintaining the crystal structure of the EU-2 zeolite; and pores having a diameter of 40 to 200 Å, wherein the volume of the pores having a diameter of 30 to 40 Å is about 0.01 to 0.06 cc/g, and the volume of the pores having a diameter of 40 to 200 Å is about 0.07 to 0.4 cc/g.

According to an embodiment, in the step b), the molar ratio of alkali cation to aluminum ($Na^+/Al_2O_3$) in the EU-2 zeolite may be about 0.1 to 0.3.

According to an embodiment, the method may further include the step of: c) substituting alkali cation in the activated EU-2 zeolite with ammonium ion.

According to an embodiment, in the step b), the molar ratio of silica/alumina in the activated EU-2 zeolite may be reduced by about 6 to 59% compared to the EU-2 zeolite before the step b) (that is, ΔSAR is 6 to 59).

A third aspect of the present invention provides a hydroisomerization catalyst, including: the activated EU-2 zeolite; and at least one metal selected from the group consisting of group VI metals and group VIII metals, wherein the at least one metal is included in the activated EU-2 zeolite in an amount of about 0.05 to 5 wt % based on a total weight of the catalyst.

According to an embodiment, the hydroisomerization catalyst may further include: a binder composed of clay or inorganic oxide.

A fourth aspect of the present invention provides a hydroisomerization method, including the step of: hydroisomerizing a hydrocarbon fraction as a feedstock in the presence of a catalyst containing activated EU-2 zeolite under the conditions of a temperature of about 200 to 500° C., a hydrogen pressure of about 1 to 200 atms, a liquid hourly space velocity (LHSV) of about 0.1 to 10 $hr^{-1}$ and a hydrogen/feedstock ratio of 45 to 1780 $Nm^3/m^3$.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
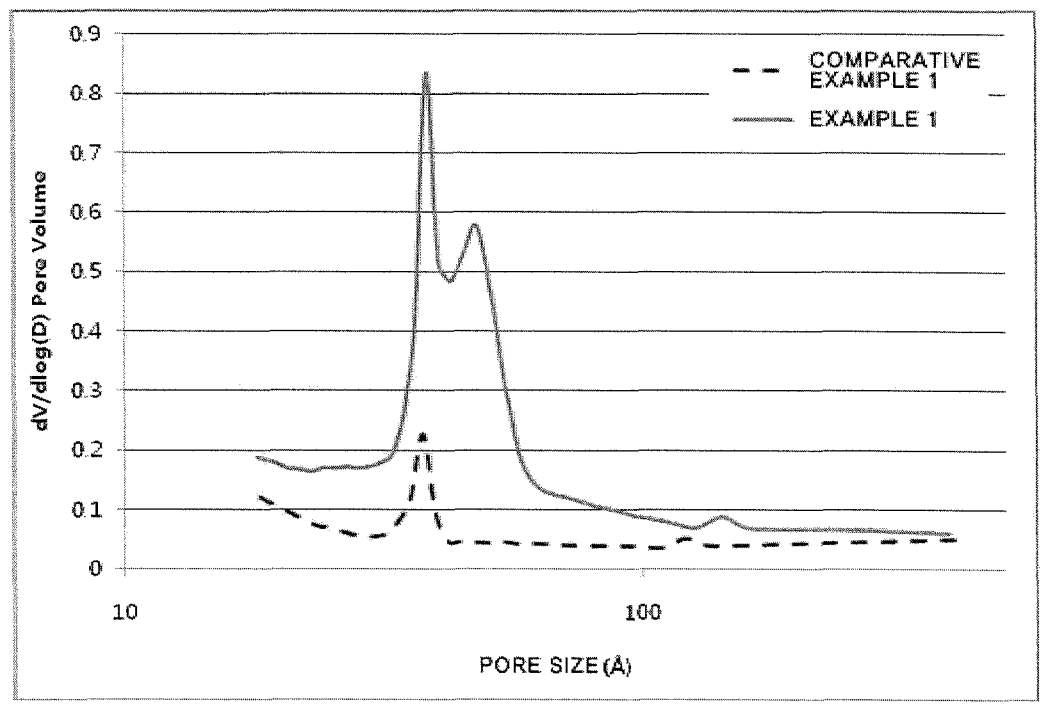
FIG. 1 is a graph showing the distribution characteristics of pore volumes of EU-2 zeolites of Example 1 and Comparative Example 1 according to pore size.

The present invention may be embodied in many different forms without departing from the spirit and significant characteristics of the invention. Therefore, the embodiments of the present invention are disclosed only for illustrative purposes and should not be construed as limiting the present invention. Hereinafter, preferred embodiments of the present invention will be described in detail with reference to the accompanying drawings. In the following description, it is to be noted that, when the functions of conventional elements and the detailed description of elements related with the present invention may make the gist of the present invention unclear, a detailed description of those elements will be omitted.

The terms used herein are defined as follows.

The term "EU-2 zeolite" is disclosed in Journal of Chemical Research, 192 (1985), and U.S. Pat. Nos. 4,741,891, 4,836,996, 4,876,412, 5,098,685 and the like. These prior art documents are used as the reference data of the present invention. Here, the present invention is described based on EU-2 zeolite, but other zeolites belonging to ZSM-48 family may also be applied.

The term "hydroisomerization reaction" means a reaction for converting at least one part of n-paraffin into iso-paraffin on a catalyst in the presence of hydrogen. The hydroisomerization reaction may be accompanied by a cracking reaction. Therefore, in order to increase the yield of a target product, it is preferable to maximize the conversion of n-paraffin into iso-paraffin by the hydroisomerization reaction while preventing the cracking reaction to the highest degree.

The term "pour point" means the lowest temperature at which liquid hydrocarbons have fluidity under given conditions.

The term "viscosity index" means a scale for measuring the change in viscosity according to temperature. The viscosity index increases with increase in the content of paraffin.

Here, the specific surface area, pore size and pore volume of zeolite are measured using a BET meter (ASAP 2020, manufactured by Micromeritics Corporation). The BET meter measures the amount of gas adsorbed on the surface of solid using the pressure change of a vacuum chamber while changing the pressure of gas at constant temperature based on BET theory. For example, after pretreatment is performed in vacuum at 350° C. for 3 hours, nitrogen ($N_2$) gas is adsorbed, and then the amount of the adsorbed nitrogen ($N_2$) gas measured, thus calculating the specific surface area, pore size and pore volume of zeolite from the BET adsorption isothermal line.

Further, the molar ratio (SAR) of silica/alumina in zeolite can be measured by a general chemical analysis technique, for example, X-ray fluorescence analysis or ICP-AES.

Activated EU-2 Zeolite

The activated EU-2 zeolite according to an embodiment of the present invention can be used as a support of a bifunctional catalyst for the hydroisomerization reaction of hydrocarbons by maintaining its intrinsic crystal structure and developing pores of 40 to 200 Å at a predetermined level by alkali treatment. That is, silicon atoms contained in the framework of EU-2 zeolite are eluted (removed), and thus pores of 40 to 200 Å are developed. In this case, when pores having a diameter of 30 to 40 Å and pores having a diameter of 40 to 200 Å are present in the predetermined volume ranges, respectively, the hydroisomerization performance of hydrocarbon fractions can be remarkably improved.

Regardless of specific theory, the reason why the activated EU-2 zeolite has excellent hydroisomerization activity for hydrocarbons (particularly, n-paraffin of C15 to C24 or more) can be presumed as follows. For example, since n-hexadecane (C16), as a reactant, is long-chain hydrocarbon and has a molecular size of about 3 to 21 Å although considering the movement of molecules, when general EU-2 zeolite (not alkali-treated) is applied to a hydroisomerization catalyst, a reaction generally takes place in the pores of 30 to 40 Å.

Since the EU-2 zeolite activated by alkali treatment, as described above, has pores of 40 to 200 Å in addition to pores of 30 to 40 Å, hydrocarbon molecules, as a reactant, can be easily permeated into pores compared to pure EU-2 zeolite, and can be effectively moved (diffused) between zeolite crystals, thereby improving reactivity. Moreover, it is presumed that hydrocarbons having a molecular size of 20 Å or more easily move and approach to a catalyst due to the increase in pores of 40 to 200 Å, thereby improving reactivity. Consequently, thy yield of a hydroisomerization product can be increased, or the reaction temperature required to accomplish the same isomerization effect can be lowered.

Further, it can be presumed that lube base oil (generally, hydrocarbons of C15 or more) having a high boiling point, for example, hydrocarbon (n-paraffin) of C24 has a molecular size of about 3 to 31 Å. Therefore, it can be assume that, considering the movement of molecules, hydrocarbon molecules can be barely introduced into pores having a pore size of 12 Å or more. In this case, pores of 40 to 200 Å effectively act on the reaction of hydrocarbon molecules in EU-2 zeolite. However, when excessively large size pores are developed during alkali treatment, that is, when pores of 200 Å or more increase at a predetermined level or more, the pores of other sizes (30 to 40 Å and 40 to 200 Å) in EU-2 zeolite are destroyed, so the contact rate of hydrocarbon molecules with active sites of zeolite is reduced, thereby deteriorating reactivity.

According to an embodiment of the present invention, the volume of pores having a diameter of 30 to 40 Å in the activated EU-2 zeolite may be present in the range of about 0.01 to 0.06 cc/g, specifically about 0.013 to 0.049 cc/g, and more specifically about 0.016 to 0.028 cc/g. Further, the volume of pores having a diameter of 40 to 200 Å in the activated EU-2 zeolite may be present in the range of about 0.07 to 0.4 cc/g, specifically about 0.077 to 0.396 cc/g, and more specifically about 0.173 to 0.368 cc/g.

Although the present invention is not limited to specific theory, when the volume of pores having a diameter of 30 to 40 Å decreases at a predetermined level or less, the pores of EU-2 zeolite itself may be destroyed even though the volume of pores having a diameter of 40 to 200 Å increases, thus deteriorating the activity of EU-2 zeolite for a hydroisomerization reaction. Therefore, it is preferred that two size types of pores be adjusted within the above volume range.

According to another embodiment of the present invention, the volume of pores having a diameter of more than 200 Å in the activated EU-2 zeolite may be adjusted in the range of about 0.1 cc/g or less, specifically about 0.085 cc/g or less, and more specifically about 0.05 cc/g or less. That is, as described above, the reason for this is that, when the pores having a diameter of more than 200 Å increase at a predetermined level or more during alkali treatment, the pores of other sizes (30 to 40 Å and 40 to 200 Å) in the activated EU-2 zeolite are destroyed.

According to still another embodiment of the present invention, the total specific surface area of the activated EU-2 zeolite may be present in the range of about 240 to 330 m$^2$/g, specifically about 260 to 315 m$^2$/g, and more specifically about 270 to 310 m$^2$/g. That is, it means that the specific surface area of the activated EU-2 zeolite is increased from the typical specific surface area (about 220 m$^2$/g) thereof before alkali treatment.

Meanwhile, the molar ratio of silica/alumina (SAR) in EU-2 zeolite is decreased by alkali treatment. The SAR of the activated EU-2 zeolite can be reduced by about 6 to 59%, specifically about 10 to 45%, more specifically about 10 to 43%, and far more specifically about 12 to 35%, compared to the SAR of non-activated EU-2 zeolite. Further, the SAR of the activated EU-2 zeolite may be present in the range of about 50 to 160, specifically about 60 to 150, and more specifically about 70 to 130.

Preparation of Activated EU-2 Zeollite

Synthesis of EU-2 Zeolite

According to an embodiment of the present invention, in advance of alkali treatment, EU-2 zeolite can be synthesized by a hydrothermal synthesis method known in the related field, and can be prepared from an aqueous reaction mixture solution including a silica source, an alumna source, a base (alkaline compound) and a template (or a structure directing agent). Generally, a zeolite material is prepared by mixing an organic template material (or a structure directing agent) with an aqueous alkaline solution containing raw materials such as silica and alumina and then hydrothermally synthesizing the mixture in a batch reactor such as an autoclave.

In this case, the characteristics of the zeolite material, such as structure, purity, crystal size and the like, depend on various variables, such as relative concentration between raw materials (silica, alumina, base, water, etc.), whether aging is conducted prior to hydrothermal synthesis, hydrothermal synthesis temperature, and whether stirring is conducted during hydrothermal synthesis. In relation to this, considering the above-mentioned variables, the hydrothermal synthesis reaction may be performed at about 150 to 180° C. (preferably about 155 to 175° C., and more preferably about 160 to 170° C.) for about 40 to 56 hours (preferably about 44 to 52 hours) until EU-2 zeolite crystals are sufficiently formed such that a reaction mixture can be uniformly reacted by supplying sufficient energy by stirring the reaction mixture using a general stirrer while heating the reaction mixture. The crystals formed by this reaction are generally purified (or filtered) and then washed with water (deionized water).

In this case, as the silica source, silicate, silica gel, colloidal silica, fumed silica, tetraalkyl orthosilicate, silicon hydroxide, precipitated silica, clay, etc. may be used. Among these exemplified silica sources, precipitated silica and silica gel can be obtained as the brand name "ZEOSIL", and colloidal silica can be obtained as the brand name "LUDOX" (for example, LUDOX HS-40 Colloidal Silica, 40 wt % suspension in water, SiO2=60.08, Sigma-Aldrich). The alumina source can be present in the form of an alumina-soluble salt. Examples of the alumina source may include sodium aluminate, aluminum chloride, aluminum alcoholate, hydrated alumina (for example, gamma alumina), pseudobohemite and colloidal alumina. Typically, commercially-available Sodium Aluminate (NaAlO$_2$), manufactured by Junsei Chemical Corporation, may be used.

The base serves as a mineralizing agent. As the base, alkali metal hydroxides, for example, sodium hydroxide, potassium hydroxide, etc., may be used.

As the template or structure direction agent (SDA), generally known organic nitrogen-containing compounds, such as alkyl amine, tetramethyl ammonium compounds, diquaternary ammonium compounds, may be used. Preferably, hexamethonium salts, particularly, hexamethonium chloride dehydrate ($[(CH_3)_3N(CH_2)_6N(CH_3)_3]Cl_2 \cdot 2H_2O$) may be used.

According to an exemplary embodiment, the reaction mixture for preparing zeolite may have the following composition (molar ratio) given in Table 1 below.

TABLE 1

|  | Wide range | Specific range | More specific range |
| --- | --- | --- | --- |
| $SiO_2/Al_2O_3$ | about 120 to 250 | about 130 to 200 | about 140 to 170 |
| $H_2O/SiO_2$ | about 16.0 to 18.0 | about 16.5 to 17.5 | about 16.8 to 17.2 |
| $OH^-/SiO_2$ | about 0.1 to 0.9 | about 0.15 to 0.5 | about 0.2 to 0.3 |
| $R/SiO_2$ | about 0.01 to 0.1 | about 0.015 to 0.5 | about 0.02 to 0.1 |
| $Na^+/SiO_2$ | about 0.01 to 0.1 | about 0.015 to 0.5 | about 0.02 to 0.1 |

Here, R is a template.

Preferably, the molar ratio of silica/alumina (SAR) in the EU-2 zeolite prepared as above may have an optimal value such that pores having a diameter of 40 to 200 Å are effectively formed in the procedure of extracting and removing silicon atoms during the subsequent alkali treatment. According to an exemplary embodiment, the SAR thereof may be about 80 to 300, specifically about 100 to 250, and more specifically about 120 to 200. In this case, the volume of pores having a diameter of 30 to 40 Å in the EU-2 zeolite may be about 0.001 to 0.05 cc/g (specifically, about 0.01 to 0.02 cc/g), whereas the volume of pores having a diameter of 40 to 200 Å may be about 0.05 cc/g or less (specifically, about 0.03 cc/g or less). Further, the volume of pores having a diameter of more than 200 Å may also be about 0.05 cc/g or less (specifically, about 0.03 cc/g or less). Therefore, pores having a diameter of 30 to 40 Å are generally distributed in the synthesized EU-2 zeolite.

In addition, the total specific surface area of the synthesized EU-2 zeolite may be about 100 to 400 m²/g, specifically about 150 to 300 m²/g, and more specifically about 210 to 250 m²/g. Preferably, the total specific surface area thereof may be about 220 m²/g.

Activation (Alkali Treatment) of EU-2 Zeolite

According to an embodiment of the present invention, the alkali treatment of the synthesized EU-2 zeolite is performed. That is, the alkali treatment thereof may be performed before or after calcining. This alkali treatment may be performed by mixing (contacting) the EU-2 zeolite (before or after calcining) with an aqueous alkali solution. The calcining step is performed in order to remove the template or structure direction agent used in the synthesis of the EU-2 zeolite. According to an exemplary embodiment, it may be advantageous that the alkali treatment be performed after synthesizing and then calcining the EU-2 zeolite.

Further, after the alkali treatment (in the case where the alkali treatment is performed after the calicining) or the calcining (in the case where the alkali treatment is performed before the calcining), it is preferred that the step of ion-exchanging the alkali-treated or calcined EU-2 zeolite with cations such as ammonium ions ($NH_4^+$) be performed in order to provide acidic characteristics for the alkali-treated or calcined EU-2 zeolite. In this case, there is an interesting point that, although EU-2 zeolite is synthesized in the range of high pH, when alkali treatment is performed, pores having a diameter of 40 to 200 Å, as described above, are formed even before calcining, thus forming activated EU-2 zeolite.

The conditions of the alkali treatment may be determined in consideration of the influence of the kind of alkaline components and the concentration of an aqueous alkali solution on the structure of EU-2 zeolite. The reason for this is that, for example, when the time taken to treat a specific aqueous alkali solution increases, silicon atoms in the crystal structure of the EU-2 zeolite are excessively eluted, thereby deteriorating the hydroisormerizion reactivity of the EU-2 zeolite.

According to an exemplary embodiment, typical examples of the alkaline components may include alkaline hydroxides and alkaline carbonates, and, particularly, alkaline hydroxides may be used. Group I metals, such as Li, Na, K, Rb and Cs, may be used as the alkaline components. Preferably, Na and/or K, more preferably Na may be used. The concentration of the aqueous alkali solution can be adjusted in the range of about 0.05 to 0.3 M, specifically about 0.1 to 0.2 M. In this case, the pH of the aqueous alkali solution may be present in the range of about 3 to 13.5, specifically about 13.1 to 13.45.

Meanwhile, the mixing (contact) temperature of the EU-2 zeolite and the aqueous alkali solution may be adjusted in the range of room temperature to 90° C., specifically about 30 to 70° C. Further, the mixing (contact) time thereof may be adjusted in the range of about 10 to 120 minutes, specifically about 30 to 90 minutes, and more specifically about 50 to 70 minutes.

As described above, alkaline components are introduced into EU-2 zeolite by alkali treatment. In this case, the alkali treatment may be performed such that the molar ratio of alkali cation to aluminum (alkali cation/alumina) in the EU-2 zeolite is present in the range of about 0.06 to 0.35, specifically about 0.1 to 0.3, and more specifically about 0.11 to 0.23. Meanwhile, when silicon atoms included in the EU-2 zeolite are removed during the alkali treatment, the SAR of the EU-2 zeolite decreases. In this case, the alkali treatment of the activated EU-2 zeolite may be controlled such that the SAR of the activated EU-2 zeolite is reduced by about 6 to 59% (that is, ΔSAR is 6 to 59), specifically about 8 to 55%, and more specifically about 10 to 45%, compared to the SAR of non-activated EU-2 zeolite.

According to an exemplary embodiment, as described above, after the alkali treatment or the calcining, the step of ion-exchanging the alkali ions contained in the EU-2 zeolite with ammonium ions may be performed. This ion exchange method is well known in the related field. Details of a typical ion exchange reaction are described in many documents including U.S. Pat. Nos. 3,140,249 and 3,140,251. These documents are used as the reference data of the present invention. In the ion exchange step, as an ammonium salt, ammonium chloride, ammonium sulfate, ammonium nitrate, ammonium phosphate, ammonium acetate and the like may be used, and, generally, ammonium nitrate may be used. The ammonium salt is used in the form of an aqueous solution, and the concentration of the ammonium salt in the aqueous solution may be present in the range of about 0.5 to 2 N, specifically, about 0.8 to 1.2 N. The ion exchange step may be performed at about 40 to 90° C., specifically, about 50 to 70° C. for about 1 to 3 hours, specifically, about 1.5 to 2.5 hours. This ion exchange step may be performed over one or more steps according to desired degree of ion exchange. That is, during the ion exchange (in the case where the ion exchange is performed two or more times) or after the ion exchange, normal procedures such as filtering, drying (for example, at about 80 to 100° C. for about 5 to 20 hours) and/or grinding may be performed.

The calcining step is generally performed under an oxygen atmosphere (for example, an air atmosphere). In this case, the calcining temperature may be present in the range of about 400° C. or more, specifically, about 500 to 700° C., and the calcining time may be present in the range of about 3 to 7 hours, specifically, about 4 to 6 hours.

Hydroisomerization Catalyst

According to an embodiment of the present invention, a hydroisomerization catalyst can be prepared by using activated EU-2 zeolite as a support of a bifunctional catalyst. In this case, the metal for hydrogenation (hydrogenation-dehydrogenation) loaded on a catalyst, which is combined with activated EU-2 zeolite, may be at least one selected from group VI and VIII metals on the Periodic Table. Examples of the metal may include Fe, Ni, Mo, Co, W, Mn, Cu, Ru, Pt and Pd. Specifically, Pt and/or Pd may be used as the metal. The hydrogenation metal or combination thereof may be included in an amount of about 0.05 to 5 wt %, specifically about 0.1 to 3 wt %, and more specifically about 0.2 to 1 wt % based on the total weight of the catalyst. In this case, as a method for supporting the metal, methods well known in the related field, such as impregnation (for example, pore volume impregnation or continuous solution impregnation), ion exchange and the like, may be used. Additionally, in order to increase the isomerization performance of the EU-2 zeolite and adjust the activity of acid sites of the EU-2 zeolite, a dopant may be added. Examples of the dopant may include halogen, phosphorus, and rare-earth elements.

Meanwhile, the hydroisomerization catalyst may be used in preparing a matrix using a well known binder together with activated EU-2 zeolite in order to improve the physical/mechanical properties thereof or perform a molding. Examples of the binder may include clay, inorganic oxides and combinations thereof. Here, examples of the inorganic oxides may include silica, alumina, titania, magnesia, germania, thoria, boria, silica-alumina, silica-magnesia, silica-zirconia, silica-thoria, and silica-titania. According to circumstances, it is preferred that the intrinsic acid sites of the activated EU-2 zeolite be not influenced by using a binder having low acidity.

Here, the activated EU-2 zeolite is milled together with the binder, and is then extruded by a general extrusion technique. In this case, the weight ratio of zeolite:binder may be adjusted in the range of about 90:10 to 30:70, specifically, about 70:30 to 50:50, but the present invention is not limited thereto.

According to an exemplary embodiment, the catalyst may be manufactured in the form of a compact (for example, an extruded product) including the activated EU-2 zeolite and the binder and supported with metal components. In this case, the support may be fabricated using a forming technique well known in the related field. For example, the support may be fabricated by extrusion (a screw extruder, a plate extruder, a ram extruder or the like can be used) and pelletization. The compact may be formed in various shapes and sizes.

Further, after the support is supported with hydrogenation metal components (typically, having a precursor form), a drying process (for example, at about 60 to 200° C.) and a calcining process (for example, at about 300 to 700° C. for about 0.5 to 20 hours, specifically, at about 400 to 600° C. for about 2 to 10 hours) may be performed.

Selectively, prior to the hydroisomerization reaction, drying, reduction, pre-sulfidation or the like may be carried out for the purpose of the activation and/or pre-treatment of the catalyst. Particularly, when precious metals are used as the hydrogenation metals, they may be reduced at a temperature of about 250 to 350° C. and a pressure of about 1 to 200 atms under a hydrogen atmosphere.

Hydroisomerization Process

According to an embodiment of the present invention, there is provided a process of converting an n-paraffin-containing feedstock (including mineralized, synthesized and/or biomass-derived feedstocks) into iso-paraffin by isomerizing the feedstock while supplying hydrogen in the presence of a catalyst containing activated EU-2 zeolite. Generally, this feedstock may include n-paraffin in an amount of about 15 wt % or more, specifically, about 40 wt % or more.

Specific examples of the feedstock may include hydrocarbon fractions having a boiling point of about 150 to 580° C. (which can be measured according to ASTM D-86 or ASTM D-2887), middle distillates (including paraffin oil and gas oil) and hydrocarbon fractions having a boiling point within the boiling point of lube base oil.

Particularly, since the activated EU-2 zeolite included in the hydroisomerization catalyst includes a large number of pores having a diameter of 40 to 200 Å, it can be effectively applied to hydrocarbon fractions of 15 or more carbon atoms (specifically, 16 to 35 carbon atoms) having a boiling point within the boiling point (about 360 to 580) of lube base oil.

Particularly, typical examples of the above-mentioned feedstock may include oil derived from a solvent refining process (for example, reffinates), partially-solvent-dewaxed oil, deasphalted oil, distillates, vacuum gas oil, coking gas oil, unconverted oil of a fuel oil hydrocracking process, and gas oil distillates. Further, the feed stock may include wax derived from Fischer-Tropsch Reaction.

According to an exemplary embodiment, the feedstock may include n-paraffin (wax component) in an amount of about 15 wt % or more, specifically, about 40 wt % or more. Further, the feedstock may include nitrogen in an amount of about 10 ppm (wt) or less (specifically about 5 ppm (wt) or less) and/or sulfur in an amount of about 10 ppm (wt) or less (specifically about 5 ppm (wt) or less).

The hydroisomerization process of the feedstock may be performed under the conditions of a temperature of about 200 to 500° C. (specifically about 220 to 450° C., and more specifically about 240 to 400° C.), a hydrogen pressure of about 1 to 200 atms (specifically about 100 to 180 atms, and more specifically about 130 to 150 atms), a liquid hourly space velocity (LHSV) of about 0.1 to 10 hr$^{-1}$ (specifically about 0.5 to 5 hr$^{-1}$, and more specifically about 1 to 2 hr$^{-1}$) and a hydrogen/feedstock ratio of about 45 to 1780 Nm$^3$/m$^3$ (specifically about 200 to 100 Nm$^3$/m$^3$, and more specifically about 480 to 530 Nm$^3$/m$^3$).

After the hydroisomerization process, the pour point of a hydrocarbon fraction (feedstock) may be lowered by about −12° C. or more, specifically, about −18° C. or more. Further, even when the feedstock is a hydrocarbon fraction having a boiling point within the boiling point of lube base oil, the viscosity index thereof may be present in the range of about 60 or more, specifically about 70 to 160, more specifically about 80 to 150, and most specifically about 120 to 140.

Further, according to an exemplary embodiment, in the hydroisomerization process, it is preferable to optimize an isormerization reaction while retarding cracking. For example, the process condition may be adjusted such that the amount of 150° C.+ distillate converted into 150° C.− distillate is 20 wt % or less, specifically about 10 wt %, and more specifically about 5 wt % or less.

Hereinafter, the present invention will be described in detail with reference to the following Examples. These Examples are set forth to illustrate the present invention, and the scope of the present invention is not limited thereto.

Comparative Example 1

Hexamethonium chloride, as a template material, sodium aluminate (Junsei Chemical Co.), as an aluminum source, Ludox-HS40 (Sigma Aldrich; colloidal silica (40 wt % suspension/water)), as a silica source, and sodium hydroxide (NaOH) were dissolved in deionized water (DI water) to prepare a raw material mixture for zeolite synthesis. The composition of the raw material mixture is given in Table 2 below.

Subsequently, the raw material mixture was introduced into a teflon-coated hydrothermal synthesis reactor, and then reacted at 165° C. for 2 days (48 hours) to obtain zeolite crystals. The zeolite crystals were sufficiently washed with distilled water, dried at 60° C. for 12 hours, and then calcined at 550° C. for 5 hours. The characteristics and crystal structure of the obtained zeolite material were analyzed, and the results thereof are given in Table 2 below. From the analysis results, it was ascertained that zeolite having a pure EU-2 crystal structure reported in conventional documents and patents and including pores having a diameter (D1) of 30 to 40 Å was obtained (refer to FIGS. 1 and 2).

TABLE 2

| EU-2 Synthesis condition | | Value | |
|---|---|---|---|
| Synthesis condition | Composition of raw material mixture (based on mol) | $SiO_2/Al_2O_3$ (=SAR) | 160 |
| | | (Si/Al) | 80.34 |
| | | $H_2O/SiO_2$ | 17.01 |
| | | $OH^-/SiO_2$ | 0.21 |
| | | $Na/SiO_2$ | 0.21 |
| | | template/$SiO_2$ | 0.02 |
| | Synthesis temperature (° C.) | | 165 |
| | Synthesis time (hr) | | 48 |
| Product | | $SiO_2/Al_2O_3$ (=SAR) | 150 |
| | | XRD pattern | EU-2 |

The hydrothermally-synthesized EU-2 zeolite was ion-exchanged with ammonium ions ($NH_4^+$) using a 1N ammonium nitrate solution. The ion-exchanged EU-2 zeolite was mixed with a binder (psuedoboehmite) at a weight ratio of 1:1, and an aqueous $[Pt(NH_3)4](NO_3)_2$ solution was impregnated into the mixture of the EU-2 zeolite and the binder such that the content thereof is 0.6 wt % based on the content of Pt. The impregnated mixture was dried at 120° C. for 3 hours, and then calcined at 500° C. for 3 hours to obtain a catalyst.

The catalyst obtained in this way was charged into a fixed-bed reactor having an outer diameter of ½ inch, activated at 260° C. for 1 hour under a hydrogen atmosphere, and then a hydroisomerization reaction experiment was carried out. In the hydroisomerization reaction experiment, n-hexadecane, as a feedstock, was introduced into the reactor by a pump at a flow rate of 1 g/hr, the hydroisomerization reaction pressure was adjusted to 30 atms, and the hydrogen feed rate was adjusted to 650 cc/hr. During the hydroisomerization reaction, the conversion ratio of n-hexadecane was also changed depending on reaction temperature, and the maximum yield of a hydroisomerization product was measured according to reaction temperature. The conditions of alkali treatment, the properties of activated EU-2 zeolite and the maximum yield of hydroisomerization product are given in Table 3 below.

Comparative Example 2

The hydrothermal synthesis (prior to ion change) of EU-2 zeolite was carried out in the same manner as in Comparative Example 1. Thereafter, activated EU-2 zeolite was prepared using an aqueous alkali solution as follow.

The hydrothermally synthesized EU-2 zeolite was mixed with a 0.05M aqueous sodium hydroxide solution, stirred at 50° C. for 1 hour by a rotary evaporator, washed with distilled water, and dried at 60° C. for 12 hours to obtain activated EU-2 zeolite. The activated EU-2 zeolite was ion-exchanged with ammonium ions in the same manner as in Comparative Example 1 to prepare a catalyst. The conversion reaction experiment of n-hexadecane was carried out using the catalyst in the same manner as in Comparative Example 1. The conditions of alkali treatment, the properties of activated EU-2 zeolite and the maximum yield of hydroisomerization product are given in Table 3 below.

Comparative Example 3

Activated EU-2 zeolite was prepared in the same manner as in Comparative Example 2, except that the conditions of alkali treatment were changed. Subsequently, an isomerization catalyst was prepared using the activated EU-2 zeolite, and then an isormerization reaction was performed. In this case, the concentration of an alkali solution used was 0.3 M, and alkali treatment time was 1 hour.

The conditions of alkali treatment, the properties of activated EU-2 zeolite and the maximum yield of hydroisomerization product are given in Table 3 below.

TABLE 3

| | Alkali treatment conditions | | | | Pore volume (cc/g) | | | Specific surface area Total $(m^2/g)$ |
|---|---|---|---|---|---|---|---|---|
| Class. | Molar ratio of $Na^+/Al_2O_3$ | pH | ΔSAR | Maximum yield (%) | $D1^1$ | $D2^2$ | $D3^3$ | |
| Comp. Ex. 1 | — | — | — | 84.44 | 0.015 | 0.032 | 0.021 | 220 |
| Comp. Ex. 2 | 0.055 | 12.98 | 5 | 84.52 | 0.060 | 0.052 | 0.039 | 314 |
| Comp. Ex. 3 | 0.33 | 13.49 | 60 | 83.53 | 0.006 | 0.464 | 0.214 | 263 |

[1]D1 (30 to 40Å)
[2]D2 (40 to 200Å)
[3]D3 (more than 200Å)

As given in Table 3 above, in Comparative Examples 2 and 3, the volume of pores corresponding to D2 size (40 to 200 Å) deviated from the range of 0.07 to 0.4 cc/g although EU-2 zeolite was alkali-treated. As such, when a catalyst was prepared from the activated EU-2 zeolite, the yield of n-hexadecane according to an isomerization reaction (Comparative Example 2) was similar to that of a catalyst prepared from the EU-2 zeolit of Comparative Example 1, or the yield of n-hexadecane according to an isomerization reaction (Comparative Example 3) was lower than that of a catalyst prepared from the EU-2 zeolit of Comparative Example 1.

Particularly, when EU-2 zeolie was extremely alkali-treated as in Comparative Example 3, unlike the EU-2 zeolte of Comparative Example 1 before alkali treatment, the pore volume of D1 size was remarkably decreased, whereas the pore volume of D2 size was rapidly increased. Further, the pores of D1 size formed in the EU-2 zeolite before alkali treatment are remarkably destroyed, and thus the volume thereof was decreased to 0.006 cc/g, whereas the volume of pores of D3 size (more than 200 Å) are greatly increased to 0.214 cc/g. Consequently, it is determined that the hydroisomerization performance of EU-2 zeolite was deteriorated due to the reduction of active sites of EU-2 zeolite. Like this, when alkali treatment is excessively performed, silicon atoms in the framework of zeolite are eluted, and thus the structure of EU-2 zeolite is destroyed, so it is required to suitably adjust the conditions of alkali treatment. In contrast, in the case of Comparative Example 2 in which the conditions of alkali treatment are mild, it is determined that these conditions do not have a great influence on the improvement in isomerization activity of the zeolite of Comparative Example 1.

Example 1

The hydrothermal synthesis of EU-2 zeolite was carried out in the same manner as in Comparative Example 1. Thereafter, the hydrothermally synthesized EU-2 zeolite was mixed with a 0.1 M aqueous sodium hydroxide (NaOH) solution under the conditions given in Table 4 below, stirred at 50° C. for 1 hour by a rotary evaporator, washed with distilled water, and dried at 60° C. for 12 hours to obtain activated EU-2 zeolite.

The activated EU-2 zeolite was ion-exchanged with ammonium ions in the same manner as in Comparative Example 1 to prepare an isomerization catalyst. The conversion reaction experiment of n-hexadecane was carried out using the catalyst in the same manner as in Comparative Example 1. Further, the maximum yield of an isomerization product according to reaction temperature was measured in the same manner as in Comparative Example 1. The conditions of alkali treatment, the properties of activated EU-2 zeolite and the maximum yield of a hydroisomerization product are given in Table 4 below together with the results of Comparative Example 1.

TABLE 4

| Class. | Alkali treatment conditions | | | Maximum yield (%) | Pore volume (cc/g) | | | Specific surface area Total (m²/g) |
| --- | --- | --- | --- | --- | --- | --- | --- | --- |
| | Na⁺/Al₂O₃ | pH | ΔSAR | | D1 | D2 | D3 | |
| Comp. Ex. 1 | — | — | — | 84.44 | 0.015 | 0.032 | 0.021 | 220 |
| Ex. 1 | 0.11 | 13.20 | 10 | 87.30 | 0.054 | 0.107 | 0.026 | 296 |

Figure 2:
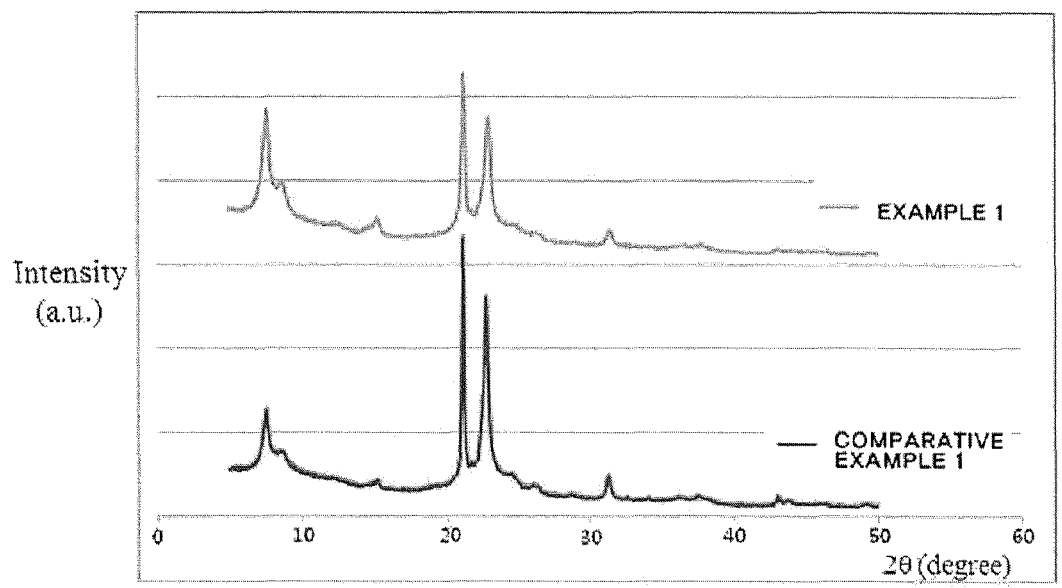
FIG. 2 is a graph showing the XRD patterns of EU-2 zeolites of Example 1 and Comparative Example 1.
Figure 3:
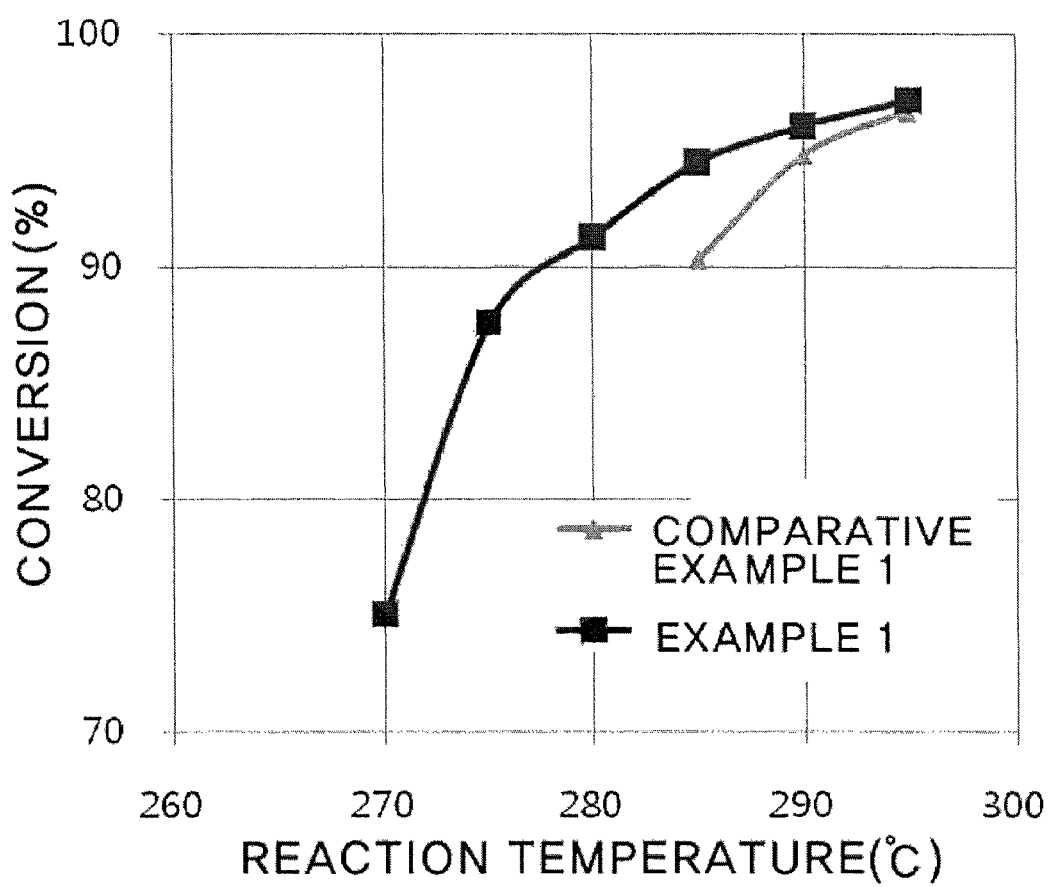
FIG. 3 is a graph showing the conversion rates of EU-2 zeolites of Example 1 and Comparative Example 1 for a hydroisomerization reaction according to reaction temperature.

Further, in the activated EU-2 zeolite of Example 1 and pure EU-2 zeolite of Comparative Example 1, the distribution characteristics of pore volume according to pore size, XRD patterns, and the conversion ratio of n-hexadecane in the hydroisomerization reaction according to reaction temperature are shown in FIGS. 1 to 3.

Referring to Table 4 above and FIG. 1, it can be ascertained that pores of D2 size as well as pores of D1 size were developed by alkali treatment, and that the specific surface area of EU-2 zeolite was rapidly increased. Further, as shown in FIG. 2, the XRD pattern of activated EU-2 zeolite is the same as that of pure EU-2 zeolite. Therefore, it can be ascertained that the crystal structure of EU-2 zeolite was not changed.

From the results of a hydroisomerization reaction, it is determined that pores of D2 size, larger than pores of D1 size, are developed in the activated EU-2 zeolite, and thus the mass transfer (diffusion) between reactants and active sites in zeolite is easily conducted, so the yield of n-hexadecane is increased at the time of the conversion reaction of n-hexadecane. Further, as shown in FIG. 3, in the case of a catalyst containing activated EU-2 zeolite, reaction temperature required to attain the same yield was lowered.

Examples 2 to 5

Activated EU-2 zeolite was prepared in the same manner as in Example 1, except that the pH of an alkali solution and the molar ratio of Na⁺/Al₂O₃ and the like were changed in the procedure of alkali treatment of the EU-2 zeolite (before ion exchange) hydrothermally synthesized in the same manner as in Comparative Example 1. Further, an isomerization catalyst was prepared using the activated EU-2 zeolite of Example 1, and the conversion reaction experiment of n-hexadecane was carried out. The conditions of alkali treatment, the properties of activated EU-2 zeolite and the maximum yield of hydroisomerization product are given in Table 5 below together with the results of Comparative Example 1 and Example 1.

TABLE 5

| Class. | Alkali treatment conditions | | | Maximum yield (%) | Pore volume (cc/g) | | | Specific surface area Total (m²/g) |
| --- | --- | --- | --- | --- | --- | --- | --- | --- |
| | Molar ratio of Na⁺/Al₂O₃ | pH | ΔSAR | | D1 | D2 | D3 | |
| Comp. Ex. 1 | — | — | — | 84.44 | 0.015 | 0.032 | 0.021 | 220 |
| Ex. 1 | 0.11 | 13.20 | 10 | 87.30 | 0.054 | 0.107 | 0.026 | 296 |
| Ex. 2 | 0.11 | 13.20 | 12 | 87.49 | 0.055 | 0.123 | 0.025 | 278 |
| Ex. 3 | 0.11 | 13.20 | 13 | 87.27 | 0.028 | 0.173 | 0.026 | 277 |
| Ex. 4 | 0.22 | 13.44 | 35 | 87.21 | 0.013 | 0.368 | 0.049 | 303 |
| Ex. 5 | 0.22 | 13.44 | 44 | 87.43 | 0.016 | 0.396 | 0.085 | 313 |

Figure 4:
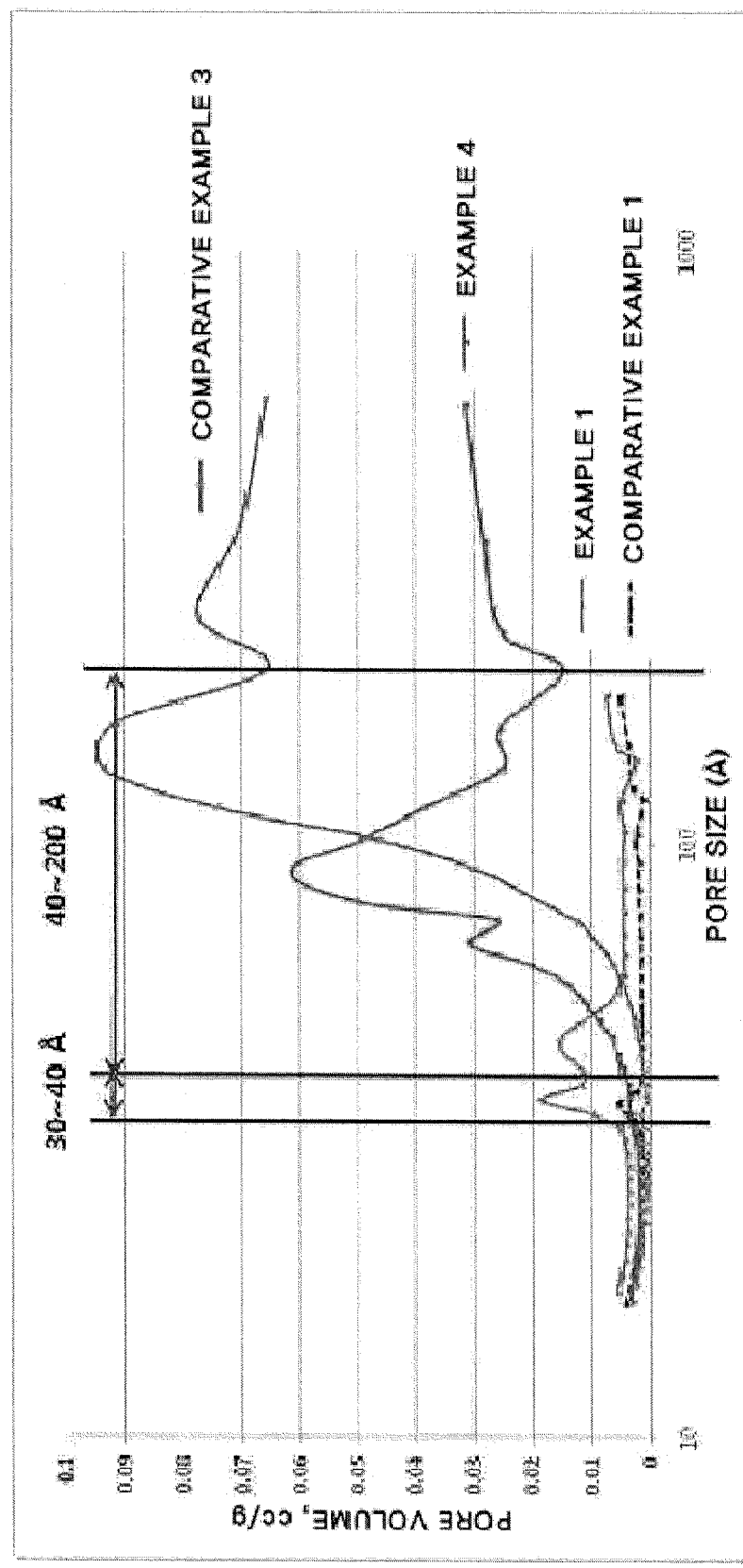
FIG. 4 is a graph showing the respective volume changes of pores of 30 to 40 Å and pores of 40 to 200 Å of EU-2 zeolites of Examples 1 and 4 and Comparative Examples 1 and 3 according to the change of an alkali treatment condition (molar ratio of $Na^+/Al_2O_3$).

Further, the volume changes of pores of D1 and D2 sizes of Comparative Examples 1 and 3 and Examples 1 and 4 according to alkali treatment conditions (molar ratio of Na⁺/Al₂O₃) are shown in FIG. 4.

Referring to Table 5 above and FIG. 4, pores of D2 size were developed by alkali treatment, and pore volume was also changed according to alkali treatment conditions. Particularly, it was ascertained that, as the molar ratio of Na⁺/Al₂O₃ and the difference (Δ SAR) in molar ratio of silica-alumina were increased under the same pH condition, pores of D2 size were further developed. Further, as pH was increased, the difference (Δ SAR) in molar ratio of silica-alumina were increased, and the volume of pores of D2 size were increased. However, it is required to notice the fact that maximum yield was not greatly changed when the volume of pores of D2 size was present in the range of 0.07 to 0.4 cc/g.

Meanwhile, in Examples 1 to 5, the results of reaction temperatures when the yield of a hydroisomerization product is 87% are given in Table 6 below.

TABLE 6

| Class. | Reaction temperatures (° C.) at maximum yield of 87% |
|---|---|
| Example 1 | 285 |
| Example 2 | 280 |
| Example 3 | 275 |
| Example 4 | 280 |
| Example 5 | 295 |

According to Table 6 above, when the volume of pores of D2 size was at a predetermined level or more, reaction temperature required to attain the maximum yield was not greatly different. However, as the degree of alkali treatment was increased, the volume of pores of D2 size was increased, but, simultaneously, the volume of pores of D3 size (more than 200 Å) was also increased. As a result, it can be ascertained that the temperature required for a hydroisomerization reaction is gradually increased. This result suggests the fact that, when the volume of pores of D2 size is excessively increased by alkali treatment, the volume of pores of D3 size is also increased, and thus the activity for hydroisomerization is gradually decreased. Therefore, it is required that the D1 and D2 sizes of pores be adjusted by adjusting the conditions of alkali treatment.

Example 6

The hydrothermal synthesis of EU-2 zeolite was carried out in the same manner as in Comparative Example 1. Thereafter, the hydrothermally synthesized EU-2 zeolite was mixed with a 0.1 M aqueous potassium hydroxide (KOH) solution under the conditions given in Table 7 below, stirred at 50° C. for 1 hour by a rotary evaporator, washed with distilled water, and dried at 60° C. for 12 hours to obtain activated EU-2 zeolite.

The activated EU-2 zeolite was ion-exchanged with ammonium ions in the same manner as in Comparative Example 1 to prepare an isomerization catalyst. The conversion reaction experiment of n-hexadecane was carried out using the catalyst in the same manner as in Example 1. Further, the maximum yield of an isomerization product according to reaction temperature was measured in the same manner as in Example 1. The conditions of alkali treatment, the properties of activated EU-2 zeolite and the maximum yield of a hydroisomerization product are given in Table 7 below together with the results of Comparative Example 1 and Example 1.

TABLE 7

| Class. | Alkali treatment conditions | | | Maximum yield (%) | Pore volume (cc/g) | | | Specific surface area Total (m$^2$/g) |
|---|---|---|---|---|---|---|---|---|
| | Molar ratio of cation/Al$_2$O$_3$ | pH | ΔSAR | | D1 | D2 | D3 | |
| Comp. Ex. 1 | — | — | — | 84.44 | 0.015 | 0.032 | 0.021 | 220 |
| Ex. 1 | 0.11 | 13.20 | 10 | 87.30 | 0.054 | 0.107 | 0.026 | 296 |
| Ex. 6 | 0.11 | 13.20 | 14 | 87.67 | 0.068 | 0.125 | 0.030 | 308 |

According to Table 7 above, it can be ascertained that the maximum yield of a hydroisomerization product is not greatly changed even when K is used as an alkali metal instead of Na.

Example 7

Whether the isomerization catalyst prepared in Example 1 can be used for manufacturing lube base oils from a range of hydrocarbon with high boiling points was evaluated by a pilot test.

A feedstock having a pour point of 48° C. was hydroisomerized (dewaxed) using the prepared isomerization catalyst under the conditions of a hydrogen pressure of 144 atms, a liquid hourly space velocity (LHSV) of 1.3 hr$^{-1}$, a hydrogen/feedstock ratio of 505 Nm$^3$/m$^3$ and a reaction temperature of 319° C. The results thereof are given in Table 8 below.

TABLE 8

| | Feedstock | Product |
|---|---|---|
| Specific Gravity | 0.8423 | 0.8423 |
| Boiling point (Distillation, D2887) | | |
| 10% | 441.4 | 414.2 |
| 90% | 523.0 | 519.0 |
| Sulfur content (wtppm) | 4.2 | <1.0 |
| Nitrogen content (wtppm) | 2.4 | <1.0 |
| Dynamic viscosity (@100° C., cSt) | 6.747 | 6.594 |
| Viscosity index | 146 | 133 |
| Pour point (° C.) | 48 | −15 |

As given in Table 8 above, it can be ascertained that the pour point of the feedstock was remarkably lowered from 48° C. to −15° C. after the hydroisomerization reaction, and thus a lube base oil product (310+C) having improved low-temperature properties could be produced. Further, it can be ascertained that the reduction rate of yield due to a cracking reaction was 9% or less, and thus the selectivity to a hydroisomerization reaction was also improved.

As described above, according to an embodiment of the present invention, compared to a conventionally known EU-2 zeolite (non-activated EU-2 zeolite), when the activated EU-2 zeolite of the present invention, wherein pores having a diameter 40 to 200 Å are developed in addition to pores having a diameter of 30 to 40 Å while maintaining its intrinsic crystal structure and the volume of each of the pores is adjusted, is used as a support of a bifunctional catalyst, there is an advantage of improving the activity of hydrocarbon to a hydroisomerization reaction (typically, a reaction for converting n-paraffin into iso-paraffin). For example, the activated EU-2 zeolite of the present invention provides the activity advantageous to the hydroisomerization reaction of hydrocarbon fractions having a boiling point of about 150 to 580° C. (typically, middle distillates and hydrocarbon fractions having a boiling point within the boiling point of lube base oil) and hydrocarbon fractions of about 15 or more carbon atoms having a boiling point within the boiling point (about 360 to 580° C.) of lube base oil. Therefore, the wide application of this activated EU-2 zeolite is expected henceforth.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of preparing an activated EU-2 zeolite, comprising the steps of:
   a) hydrothermally synthesizing an EU-2 zeolite; and
   b) activating the EU-2 zeolite by bringing the EU-2 zeolite into contact with an aqueous alkali solution before or after calcining the EU-2 zeolite,
   wherein the activated EU-2 zeolite comprises:
   pores having a diameter of 30 to 40 Å while maintaining a crystal structure of the EU-2 zeolite; and
   pores having a diameter of 40 to 200 Å,
   wherein a volume of the pores having a diameter of 30 to 40 Å is 0.01 to 0.06 cc/g, and a volume of the pores having a diameter of 40 to 200 Å is 0.07 to 0.4 cc/g.

2. The method of claim 1, wherein, in the step b), a molar ratio of alkali cation to aluminum ($Na^+/Al_2O_3$) in the EU-2 zeolite is 0.1 to 0.3.

3. The method of claim 1, further comprising the step of c) substituting alkali cation in the activated EU-2 zeolite with ammonium ion.

4. The method of claim 1, wherein, in the step b), a molar ratio of silica/alumina in the activated EU-2 zeolite is reduced by 6 to 59% compared to the EU-2 zeolite before the step b).

5. The method of claim 1, wherein, in the step a), a molar ratio of silica/alumina in the hydrothermally synthesized EU-2 is 80 to 300.

6. The method of claim 1, wherein, in the step a), a volume of the pores having a diameter of 30 to 40 Å in the hydrothermally synthesized EU-2 zeolite is 0.01 to 0.05 cc/g, and a volume of the pores having a diameter of 40 to 200 Å therein is 0.05 cc/g or less.

7. The method of claim 1, wherein, in the step a), a total specific surface area of the hydrothermally synthesized EU-2 zeolite is 210 to 250 $m^2/g$.

8. The method of claim 1, wherein the alkali is Na, K or a combination thereof.

9. The method of claim 8, wherein the aqueous alkali solution has a concentration of 0.05 to 0.3 M and a pH of 13.1 to 13.45.

* * * * *

UNITED STATES PATENT AND TRADEMARK OFFICE
CERTIFICATE OF CORRECTION

PATENT NO. : 9,782,760 B2
APPLICATION NO. : 15/605156
DATED : October 10, 2017
INVENTOR(S) : Yoon Kyung Lee et al.

It is certified that error appears in the above-identified patent and that said Letters Patent is hereby corrected as shown below:

On the Title Page

Under (71) Applicant:
Please replace the second applicant name "SK LUBRICANTS CO., LTD., Seoul (KR)" to "SK ENMOVE CO., LTD., Seoul (KR)"; and Under (73) Assignee:
Please replace the second assignee name "SK LUBRICANTS CO., LTD., Seoul (KR)" to "SK ENMOVE CO., LTD., Seoul (KR)".

Signed and Sealed this
Thirteenth Day of August, 2024

Katherine Kelly Vidal
*Director of the United States Patent and Trademark Office*